United States Patent
Sweeney et al.

[11] Patent Number: 5,856,533
[45] Date of Patent: Jan. 5, 1999

[54] HIGH EFFICIENCY HEAT AND MASS TRANSFER FOR VAPOR PHASE HETEROGENEOUS REACTIONS

[75] Inventors: Joshua Brien Sweeney, Katonah, N.Y.; Roger William Day, Southbury, Conn.; Deepak Lumba, Mohegan Lake, N.Y.

[73] Assignee: Praxair Technology, Inc., Danbury, Conn.

[21] Appl. No.: 580,216

[22] Filed: Dec. 28, 1995

[51] Int. Cl.$^6$ .................................................. C07D 301/03
[52] U.S. Cl. ........................ 549/523; 549/534; 549/533; 549/532
[58] Field of Search ................... 549/523, 534, 549/532, 533

[56] References Cited

U.S. PATENT DOCUMENTS

| | | | |
|---|---|---|---|
| 2,985,668 | 5/1961 | Shingu | 549/533 |
| 3,957,690 | 5/1976 | Bobolev et al. | 252/462 |
| 4,228,034 | 10/1980 | Butler et al. | 252/430 |
| 4,263,448 | 4/1981 | Leacock | 560/246 |
| 4,578,112 | 3/1986 | Mori et al. | 75/108 |
| 4,919,849 | 4/1990 | Litz et al. | 261/36.1 |
| 5,132,099 | 7/1992 | Hiramatsu et al. | 423/584 |
| 5,149,868 | 9/1992 | Drent | 562/497 |
| 5,210,319 | 5/1993 | Chuang et al. | 562/546 |

OTHER PUBLICATIONS

Oxidation of Sulfur Dioxide on Water—Repellent Activated Carbon—Goto et al., Chem. Eng. Comm. 1987, vol. 60, pp. 253–269.

Optimazation of Structure of Lyophobized Catalysts–Shkol'nikov et al., Institute of Electrochemistry, Academy of Sciences of the USSR, vol. 20, No. 3, pp. 768–772, May–Jun., 1979.

Catalyzed Isotopic Exchange between Hydrogen and Water Vapor over Supported Platinum—Rolston et al., Catalysis on the Energy Scene, pp. 365–372, 1984.

*Primary Examiner*—C. Warren Ivy
*Assistant Examiner*—Lyman H. Smith
*Attorney, Agent, or Firm*—Bernard Lau

[57] ABSTRACT

Heterogeneous vapor phase oxidation and other reactions are carried out at the surface of a solid catalyst, with both gaseous reactants and the solid catalyst being dispersed in a recirculating liquid solvent. Reaction and product absorption are combined into a single processing step, with enhanced catalyst performance, and product selectivity and product yields, enhanced mass and heat transfer characteristics and reduced risk of forming explosive mixtures in the course of a particular reaction.

7 Claims, 3 Drawing Sheets

HIGH EFFICIENCY HEAT AND MASS TRANSFER FOR VAPOR PHASE HETEROGENEOUS REACTIONS

BACKGROUND OF THE INVENTION

1. Field of the Invention

The invention relates to vapor-phase heterogeneous reactions. More particularly, it relates to the dispersing of gases and solids in a liquid phase, reacting the vapor-phase components in the presence of a solid catalyst, and recovering the desired reaction product from either the liquid or vapor streams exiting the reactor.

2. Description of the Prior Art

Heterogeneous vapor-phase reactions are used to produce many large volume organic and inorganic chemicals. Examples of vapor-phase processes include oxidation, ammoxidation, and oxychlorination of olefins, alkanes, and inorganic species to yield a variety of chemicals, e.g. acrylic acid, acrylonitrile, ethylene dichloride, ethylene oxide, hydrogen peroxide, maleic anhydride, methanol, phthalic anhydride, propylene oxide, vinyl acetate and formaldehyde. In commercial processes, these vapor-phase reactions are conducted in fixed-bed or fluidized-bed (two-phase) reactors.

Although no two processes are exactly alike, commercial versions of vapor-phase processes typically possess at least one characteristic, i.e., a dilute reaction stream. The actual volume fraction of the process stream entering the reactor that is converted to products is typically small. The remainder of the stream consists of inerts and unconverted reactants. Consequently, process equipment associated with reactor process stream, the recycle stream, and product recovery and purification streams must be sized to accommodate the combined flow of reacting and nonreacting species.

The excess diluent represents a process "inefficiency" that adds to fixed capital and operating costs associated with the processes. The requirement for excess diluent arises from several process constraints inherent in conventional fixed-bed and fluidized-bed vapor-phase reactor operations. These constraints include:

1. Limitations due to inadequate rates of heat transfer to remove heat of reaction from catalyst particles:

Vapor-phase oxidations are typically highly exothermic reactions. Reaction rates are limited by the rate at which heat can be removed from the solid catalyst. Rapid reaction rates or poor rates of heat transfer result in generation of catalyst hot spots, which reduce product yields and catalyst lifetimes.

2. Limitations due to conversion-selectivity trade-offs:

Frequently, in heterogeneous vapor-phase oxidations, as the extent of reaction, i.e., conversion, increases, the catalyst selectivity to the desired product decreases. Loss in selectivity is often due to side and secondary reactions forming undesirable by-products, e.g. carbon dioxide. In economic terms, these trade-offs balance effectiveness of raw materials utilization and, in some cases, the size of recycle streams.

3. Limitations in feed compositions due to flammability and explosion hazards:

Flammable compositions of mixtures containing oxygen and hydrocarbons or other combustibles are demarcated by upper and lower flammability limits. Fixed-bed vapor-phase oxidation processes are typically designed to ensure that the compositions of all process streams lie outside the flammable region to avoid explosion hazards.

These limitations are particularly important in fixed-bed processes. In fluidized-bed processes, heat removal from the catalyst is much improved over fixed-bed designs, and explosion risks are considerably reduced by separating the organic and air feed streams and operating without recycle. Fluidized-bed processes typically run at very high conversion of organic reactant and relatively low conversion of oxygen. However, like their fixed-bed counterparts, they suffer from excess inerts in the reactor process stream. Since oxygen efficiency is sacrificed to achieve high conversion of organic reactant, these processes can not tolerate the relatively high cost of the needed oxygen, and instead use feed air as the oxygen source.

A new reactor development that eliminates heat transfer limitations, reduces or eliminates the need for excess inerts, and ensures safe operation could provide significant savings in the capital equipment and operating costs associated with chemical manufacture.

There are two classes of prior art relating to vapor phase reactions, one related to conventional two-phase reactor systems, and the other related to three-phase reactor systems. The two-phase systems cannot fully address all three issues raised above.

In general, two-phase reactor designs solve the problems of flammability and heat removal by dilution of the reaction stream. By utilizing inert components or operating at low conversions with large recycle streams, the composition of the reaction stream can be maintained outside the flammable region. This dilution using inerts and unconverted reactants in the recycle stream also serves to mitigate catalyst heating effects by reducing the heat of reaction per unit volume of feed.

Heat transfer constraints can also be significantly reduced by utilizing fluidized-bed designs in preference to fixed-bed designs. Smaller catalyst particle size and higher solid-vapor heat transfer coefficients associated with fluidized-bed designs both contribute to the improved performance. However, trade-offs also pertain with respect to fluidized bed designs. Backmixing, which can lead to reduced catalyst selectivity, often results in lower reaction yields and higher rates of production of undesired reaction products.

Three-phase reactors offer significantly better heat transfer than is obtainable using two-phase reactors. Higher rates of heat removal are achieved by contacting the catalyst directly with a liquid solvent.

Three-phase reactors come in several forms: (a) fixed beds, either trickle-bed or bubble-bed reactors, depending on whether the vapor phase is continuous or not; (b) ebullated-bed reactors, the three-phase equivalent to a fluidized-bed reactor; and (c) slurry reactors in which the catalyst and vapor phases are dispersed in the liquid phase, either with or without forced convection. The predominant application of three-phase reactors has been to liquid-phase hydrogenations, although some liquid-phase oxidations have also been proposed.

In three-phase systems, the distinction between vapor-phase and liquid-phase heterogeneous catalysis is not entirely obvious since both phases coexist with the solid catalyst. It is possible, however, to distinguish between vapor-phase and liquid-phase catalytic processes in these three-phase systems, based on the mass transfer mechanisms and the resultant reaction rates. If the vapor-phase reactants must diffuse through the liquid to reach the active catalyst sites, the overall reaction rates will be much slower than if mass transfer proceeds through the vapor phase. Thus, liquid-phase processes are characterized by much lower space velocities and slower reaction rates than vapor-phase processes.

Several three-phase, liquid-phase oxidation processes using fixed-bed and slurry reactor configurations are disclosed in the prior art. These include, for example, carbonylation (Drent, U.S. Pat. No. 5,149,868), direct oxidation of hydrogen to hydrogen peroxide (Hiramatsu et al., U.S. Pat. No. 5,132,099) aqueous-based oxidations and reductions (Mori et al., U.S. Pat. No. 4,578,112), and olefinic oxidation to epoxides (Shingu, U.S. Pat. No. 2,985,668 and Bobolev et al. U.S. Pat. No. 3,957,690). These processes remove the heat transfer limitations, and in many cases, provide yields and selectivities superior to commercially practiced technology. They have failed to achieve commercial significance because, as liquid-phase processes, they do not generate commercially acceptable rates of reaction.

Reaction rates comparable to vapor-phase processes have been achieved recently in three-phase reactors by using non-wetted support material. On such supports, the solvent does not capillary condense in the pores of the support, and the reactants have direct access to the active catalyst sites by vapor-phase transport without the additional mass transfer resistances associated with absorption and diffusion in the liquid phase.

Non-wetted catalyst supports are well-known in the literature. Initially developed for catalytic exchange of deuterium between hydrogen gas and water by Stevens, Canadian Patent No. 907292, and Butler et al., U.S. Pat. No. 4,228,034, and for redox reactions in aqueous systems by Shkol'nikov et al., Kinetica i Kataliz 20, 768–772 (1979), support materials were treated with teflon to make them hydrophobic. Virtually any conventional catalyst support can be rendered hydrophobic by such treatment, e.g. silicas, aluminas, titanium dioxide, and others. Additionally, a variety of other hydrophobic supports including fluorinated carbons, porous polymeric resins, and high silica zeolites have been disclosed in the literature, e.g. Rolston et al. Catalysis on the Energy Scene, and Kaliaquine and Mahey, Eds., Elsevier, 1984.

Hydrophobic, i.e., non-wetted, supports have been tested in three-phase trickle-bed reactors and exhibit vapor-phase reaction characteristics. Some representative examples include teflon-treated activated carbon catalyst supports used in fixed-bed reactors to oxidize $SO_2$ in aqueous solutions (Goto and Morita, Chem. Eng. Commun. 60, 253–259, 1987). A fluorinated carbon is employed in a trickle-bed reactor used to oxidize organic contaminants in industrial wastewaters (Chuang et al. Ind. Eng. Chem. Res. 31, 2466–2472, 1992). Several different supports, including a styrene divinylbenzene copolymer, a fluorinated carbon, and silicalite, are used as supports for direct partial oxidation of olefins to carboxylic acids (Chuang and Fu, U.S. Pat. No. 5,210,319).

For purposes hereof, the term "non-wetted" as applied to a catalyst support/solvent combination is determined by adsorption and capillary condensation behavior, and not the applicable contact angle. The only requirement of the support is that the active component must be accessible to the reactants via transport through the vapor phase alone, i.e., at reactor conditions, the solvent must not block the access of the reactants by condensing in the pores of the support.

The three-phase reactor processes described in the prior art provide better heat transfer than conventional vapor-phase processes due to the higher heat capacity of the liquid phase. They also provide for in situ product recovery in the liquid phase. However, there are two significant problems with current three-phase reactor approaches as applied to vapor phase heterogeneous catalysis.

The first problem in inherent in trickle-bed (fixed-bed) designs utilizing hydrophobic catalyst supports in vapor-phase oxidation processes. The catalyst support must be hydrophobic to ensure vapor-phase reaction rates. It must also be intimately contacted with liquid to remove the heat and recover reaction products. For example, in trickle-bed reactors, the support catalysts are bonded to ceramic packing. A solvent flows through the column with the gas and contacts the catalyst and removes the oxidation product and the heat of reaction. However, if the support is hydrophobic, liquid flow will tend to be characterized by liquid rivulets with large portions of the catalyst bed remaining dry. Consequently, heat and mass transfer rates will be low, resulting in catalyst overheating and inefficient product recovery.

The second serious limitation of this approach is that such trickle-bed processes are co-continuous in the liquid and vapor phases. Consequently, there is significant risk of explosion if operating within the flammability limits. To eliminate explosion hazards, such processes, as described in the prior art, use excess reactant or inert species to dilute the reactive species and minimize the risk of explosion.

There remains in the art, therefore, a need for further development in three-phase reactor processes and systems. Such development will desirably overcome the two significant problems referred to above with respect to vapor-phase heterogeneous catalysis.

It is an object of the invention, therefore, to provide an improved reactor system and process for the carrying out of vapor phase heterogeneous reactions.

It is another object of the invention to provide an improved reactor system and process for the carrying out of non-wetted solid catalyst, vapor-phase heterogeneous reactions.

With these and other objects in mind, the invention is hereinafter described in detail, the novel features thereof being particularly pointed out in the appended claims.

SUMMARY OF THE INVENTION

A dispersed-phase, forced-entrainment reactor configuration is used to disperse a non-wetted solid catalyst and vapor-phase reactants in a recirculating liquid solvent. The vapor phase reactants and the solid catalysts both exist as dispersed phases in the recirculating liquid medium, which does not directly participate in the reaction. The high degree of dispersion obtained provides large vapor-solid, vapor-liquid and solid-liquid interfacial areas necessary for efficient interphase heat and mass transfer. It also provides the basis for improved efficiency of heterogeneous vapor-phase catalytic processes.

BRIEF DESCRIPTION OF THE DRAWINGS

The invention is further described herein with reference to the accompanying drawings in which.

DETAILED DESCRIPTION OF THE INVENTION

Figure 1:
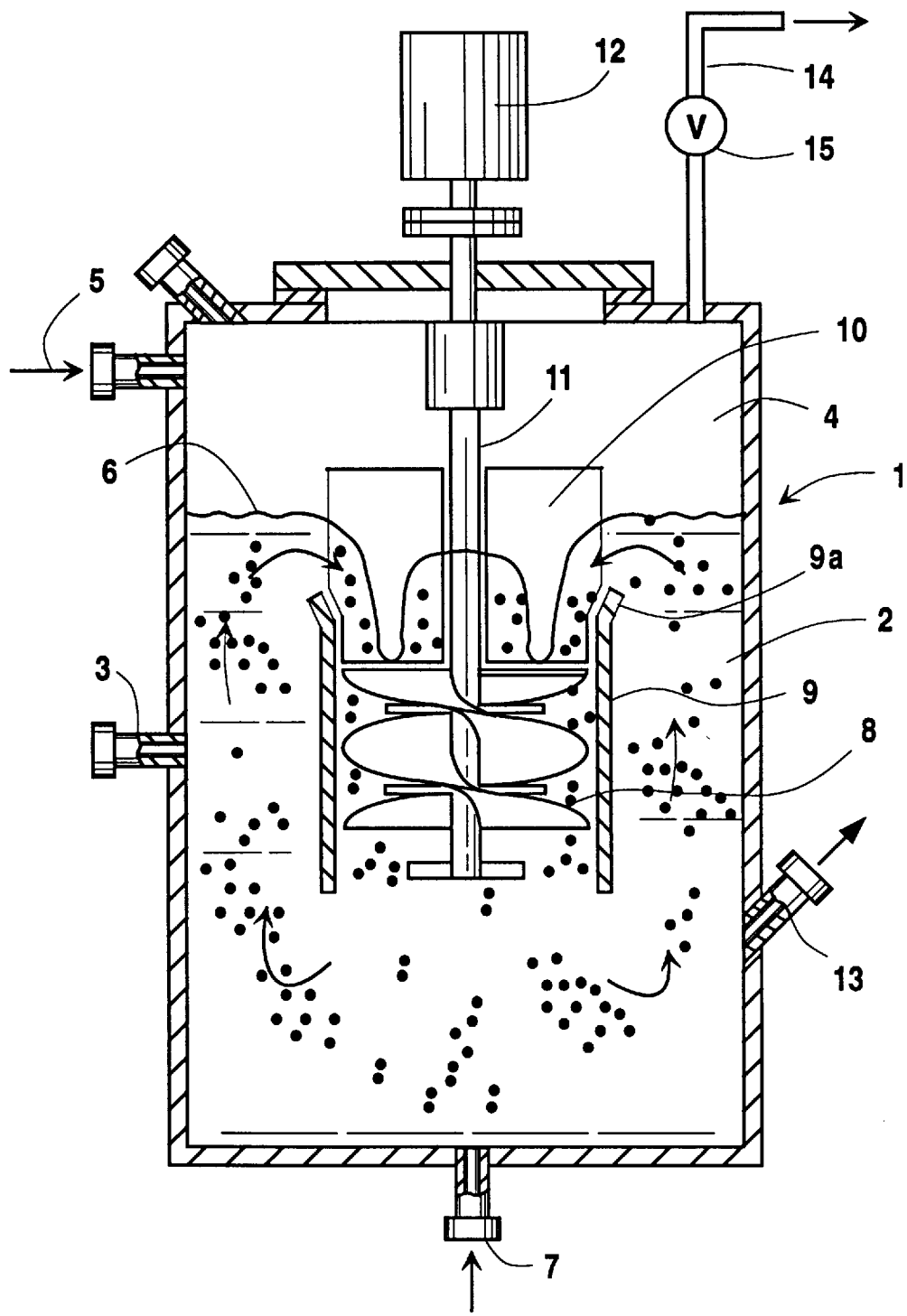
FIG. 1 is a schematic side elevational view of a reactor vessel adapted for the practice of an embodiment of the invention.

The objects of the invention are accomplished by achieving significantly larger interfacial areas between vapor and solid, vapor and liquid, and solid and liquid, thereby promoting interphase transport between the three phases employed in vapor phase heterogeneous reactions. Although such reactions can and have been performed in three-phase trickle-bed reactors, as shown by the Chuang and Fu patent U.S. Pat. No. 5,210,319 referred to above, the interfacial areas generated in the practice of the invention are significantly larger than those generated by the prior art approach. The result is higher rates of reaction, higher rates of heat removal from the catalyst, and, if applicable, higher rates of product absorption into the liquid phase. The dispersed-phase, forced-entrainment reactor configuration of the invention also provides enhanced dispersion of the catalyst and vapor phases, intimate contact of these phases with each other and with the liquid phase, and an effective internal recycle of the phases.

The invention effectively eliminates explosion hazards associated with reaction operations within the flammable range of compositions by dilution of a different type than that employed in the prior art. Instead of diluting the vapor-phase stream with added reactant or inert material, the reactants are diluted by being dispersed as fine bubbles in the liquid phase. Consequently, the amount of hydrocarbon fuel present in any one gas bubble is infinitesimal. Even if a bubble were to ignite, the ignition would be contained on a microscopic scale, with the heat evolved by the ignition of an individual bubble being rapidly dissipated in the vast thermal reservoir provided by the recirculating solvent. As a result, the invention provides for safe operation within the flammability limits, and no vapor-phase diluents need be added to avoid explosion hazards.

The small catalyst particle size, excellent dispersion, the high heat capacity of the liquid phase, and energetic mixing associated with the dispersed-phase, forced-entrainment reactor of the invention provide improved heat transfer over conventional vapor-solid approaches and over three-phase reactor designs of the prior art, which provide less energetic mixing, and, which, in the use of three-phase fixed-bed arrangements, employ much larger catalyst particles. As a result, more active catalyst can be utilized in the practice of the invention, and reaction temperatures can be reduced.

The high efficiency oxidation process of the invention, using a dispersed phase, forced-entrainment reactor as herein described, has several unique features or elements that improve the conversion-selectivity performance of the reaction process. The fine dispersion, intimate contact, and energetic mixing associated with said dispersed-phase, forced-entrainment reactor provide fast mass transfer of the oxidation products from the catalyst, through the vapor, to the liquid phase, preventing secondary reactions that degrade product selectivities. Operating with a high activity catalyst at lower temperatures also tends to improve selectivity by favoring the desired reaction over side reactions, so as to generate, more completely, the desired oxidation products.

At the heart of the subject invention is the improved interphase transport provided by the dispersed-phase, forced-entrainment reactor systems employed. Specifically, the concentric vertical draft tube, and desirably, flow baffling, employed establish the flow recirculation path, and the impeller means employed, having both pumping and dispersing elements, generates the desired three-phase flow and the large interfacial areas between the vapor and solid phases, and between the vapor and liquid phases, and the solid and liquid phases. The large interfacial areas, combined with the turbulent flow field created by said draft tube, baffling and impeller means configuration, provide excellent heat removal from the solid catalyst, rapid vapor-phase transport of reactants to catalyst, and efficient absorption of the reaction products into the liquid phase, if desired. To achieve the rapid vapor-phase transport of the reactants to the catalyst noted above, a non-wetted or hydrophobic catalyst support must be used.

Two beneficial process effects that are generated by the enhanced transport in the dispersed-phase reactor design are associated with improvements in catalyst performance. Dispersing the solid catalyst in a liquid phase prevents catalyst overheating and sintering of the active catalyst components, which results in a loss of catalytic activity. Better temperature control also improves catalyst selectivities because the selective, or desired, partial oxidation pathway is favored at lower temperatures. In addition, dispersing the vapor-phase reactants in the liquid phase along with the catalyst provides a method for removing the partial oxidation products by absorption in the liquid phase. By preventing subsequent oxidation of the partial oxidation products, the dispersed phase reactor again improves process selectivities.

The other beneficial aspect of the dispersed-phase design is unrelated to mode of operation. By introducing the reactants as a dispersed phase, hazards associated with flammability and detonation are eliminated. Thus, reactant concentrations closer to reaction stoichiometry can be utilized.

The high-efficiency oxidation process for heterogeneous vapor-phase catalysis and subsequent product recovery, as herein described and claimed, utilizes a convenient device for dispersing gases and solids in liquids. The device comprises a vessel, draft tube, impeller, flow baffles and ports for feed and product streams adapted for continuous processing operations. In the embodiment of the invention shown in FIG. 1 of the drawings, a reactor vessel, represented by the numeral 1, contains a body of liquid, i.e., solvent and catalyst 2 introduced into reactor vessel 1 through inlet 3, with one reactant drawn into the liquid from the overhead gas phase and the second reactant injected directly into the liquid below the liquid surface. Thus, a first gaseous reactant passes into the overhead gas phase through inlet line 5, and the second gaseous reactant is injected directly into the hollow surface 6 thereof, through inlet line 7. By thus separating the gaseous feed streams, the explosion hazards associated with premixed gases is avoided. Impeller means 8 is positioned in a hollow draft tube 9 positioned to draw one reactant from the overhead gas phase and to facilitate a recirculating flow pattern in which a gas bubble-solvent-catalyst solid mixture is passed downward through hollow draft tube 9 and upward in the space between said hollow draft tube 9 and the inner walls of reactor vessel 1. Baffle means 10 are conveniently positioned to facilitate the passage of the gas bubble-solvent-catalyst solid mixture downward into the top of draft tube 9. Impeller means 8 has drive shaft 11 extending upward for connection to suitable overhead driving means 12. Hollow draft tube 9 desirably includes a conically flared portion 9a at the upper end thereof, to further facilitate the flow of the gas bubble-solvent-catalyst mixture into hollow draft tube 9 for downward passage therein. Reaction product is withdrawn from reactor vessel 1 through product outlet means 13. A gas vent line 14 including valve 15 is positioned so as to vent gases from overhead gas phase 4. The optimal location of subsurface injection of the second reactant depends on the particular operating conditions in reactor vessel 1, such as the flow circulation patterns pertaining therein. The second gaseous feed inlet should preferably be located at a position ensuring complete mixing of the gaseous phases, desirably at the top of draft tube 9 or, as illustrated in FIG. 1, at the bottom of said draft tube 9, i.e., inlet line 7, so as to mix the gaseous reactants at points of high turbulence in the recirculating flow created by impeller means 8.

In the embodiment of the invention illustrated in FIG. 2 of the drawings, each feed gas is separately passed into the solvent-catalyst mixture in the reactor vessel below a gas containment baffle. In this manner, it is found that the feed rate of each gaseous reactant can be controlled independently of the other and independently of the rotational speed of the impeller means. Reactor vessel 20 contains a body of liquid, i.e., solvent, and solid catalyst 21 maintained in a recirculating flow pattern by impeller means 22 contained in hollow draft tube 23. As in the FIG. 1 embodiment, baffle means 24 and a conically flared upper portion 23a of hollow draft tube 23 are desirably provided to facilitate the passing of the gas bubble-solvent-catalyst solid mixture downward in hollow draft tube 23 and upward outside said draft tube. Impeller means 22 has drive shaft 25 extending upward to overhead drive means 26. In the FIG. 2 embodiment of the invention, gas containment baffle 27 is provided to separate the recirculating flow pattern of gas bubble-solvent-catalyst 21 from a quiescent zone 28 of liquid, having a liquid surface 29 with overhead gas phase 30, in said reactor vessel 20. It will be appreciated that fluid communication is maintained between the main body of recirculating liquid, and quiescent zone 28 through opening 31 in baffle 27, with said baffle 27 nevertheless serving to minimize passage of bubbles containing gaseous reactants to the quiescent zone and overhead gas phase 30. One reactant, e.g. oxygen, is injected directly into recirculating body of liquid and catalyst 21 through injection line 32. A second reactant, e.g. hydrocarbon feed, is separately injected directly into said recirculating body through injection line 33. An inert gas, e.g. nitrogen, flush if passed into overhead gas phase 30 through line 34 to assure against the formation of an explosive mixture in said overhead gas phase, and a vent line 35, containing valve 36, is provided to vent gases from said overhead gas phase 30. Thus, a low flow rate of nitrogen may be required and can be employed to control the composition of gas in the overhead gas phase to prevent an accumulation of explosive mixtures of unreacted hydrocarbon and oxygen in overhead gas phase 30.

Figure 2:
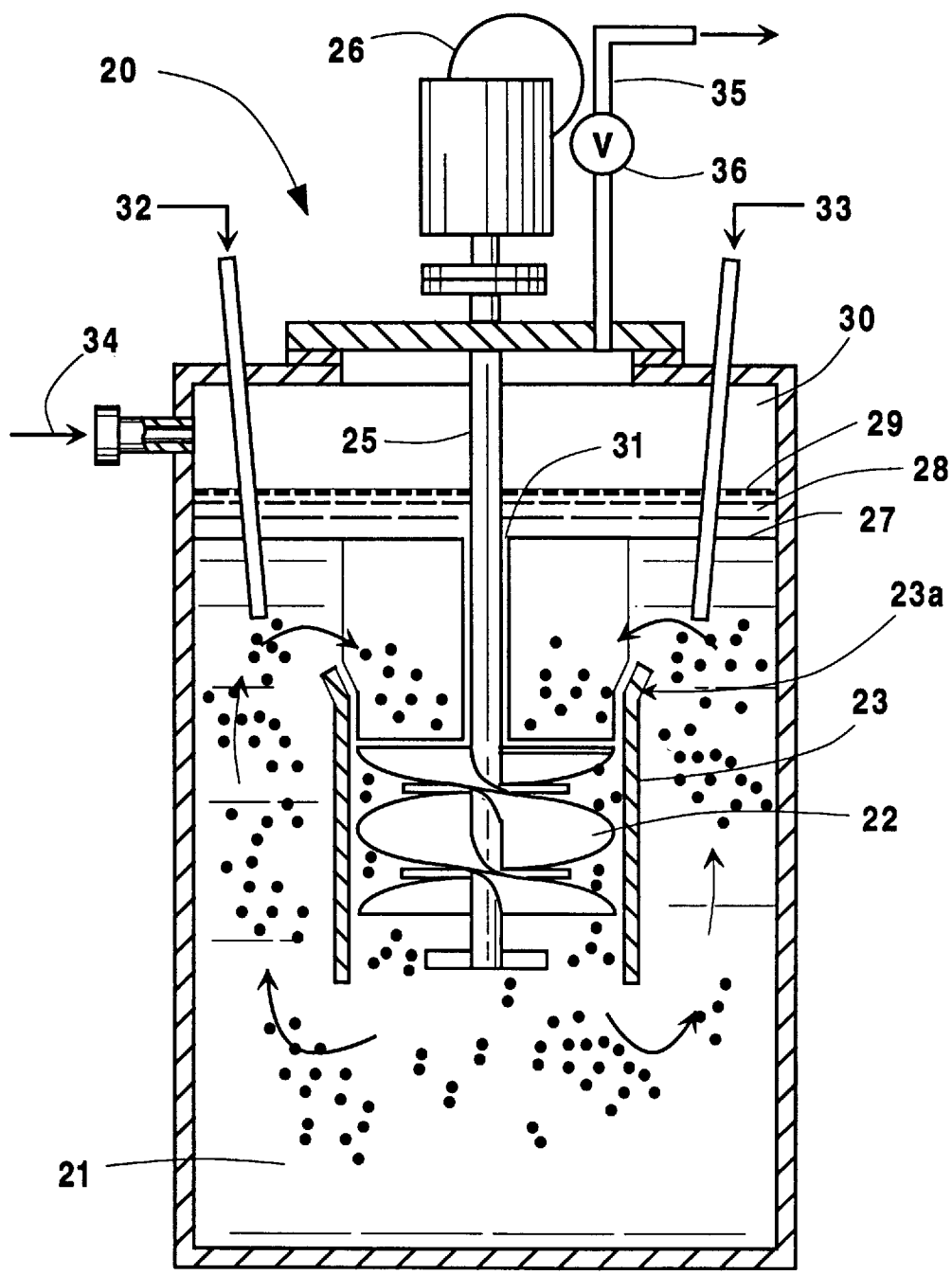
FIG. 2 is a schematic side elevational view of a reactor vessel adapted for the practice of another embodiment of the invention.

To ensure optimal mixing and dispersion of reactants, a preferred injection point of the reactant feed streams is above the draft tube, as shown in FIG. 2, so that the reactants are immediately drawn down by impeller means 22, rapidly mixed and dispersed as fine bubbles.

Figure 3:
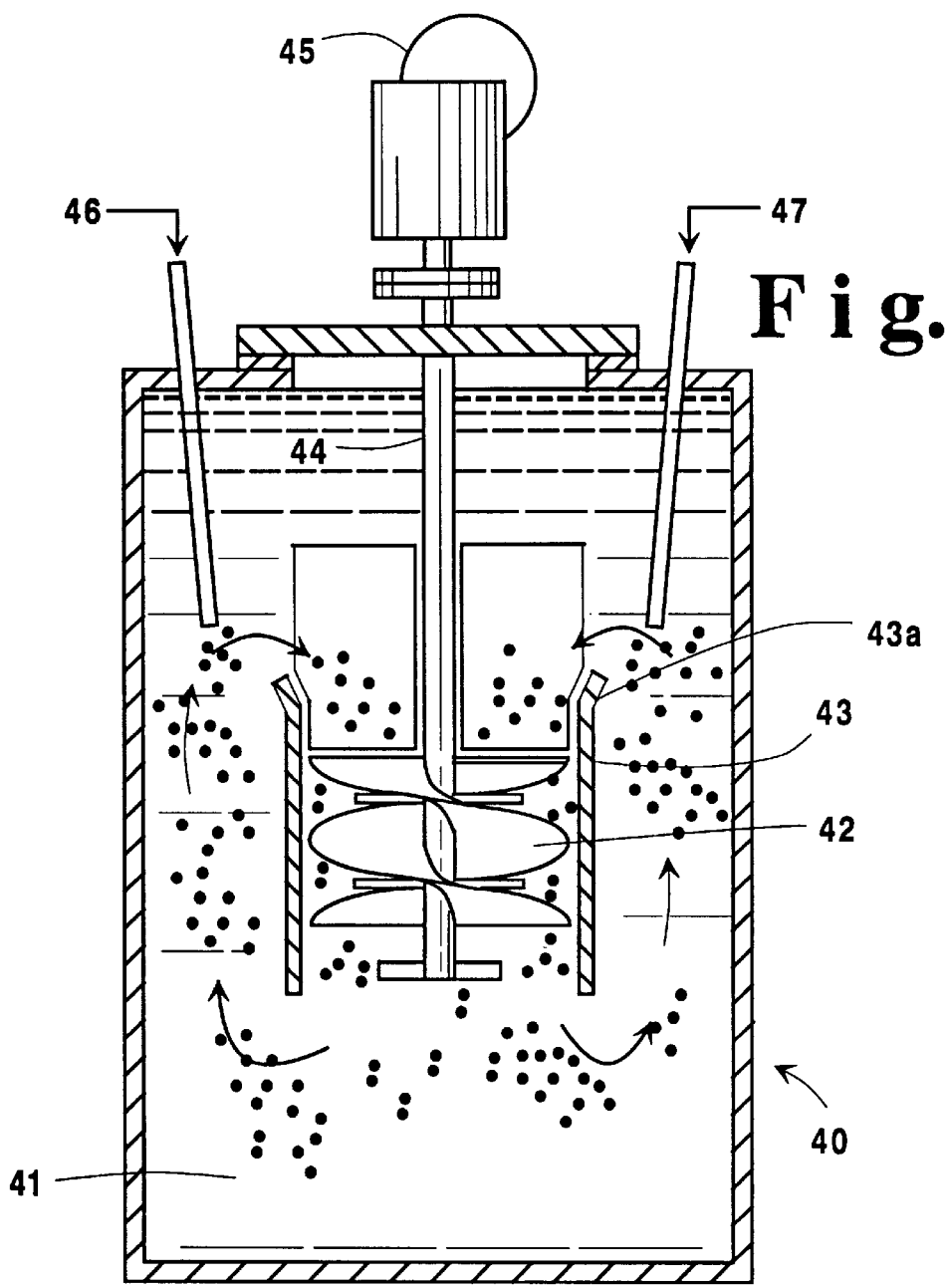
FIG. 3 is a schematic side elevational view of a variation of the reactor vessels of FIGS. 1 and 2 adapted for use in the practice of the invention.

Another embodiment of the invention is illustrated in FIG. 3 of the drawings. In this embodiment, the containment baffle of the FIG. 2 embodiment and the drawing of reactant gas from the overhead gas phase, as by a vortex action of the impeller means, are not employed, and a zero-head space approach is employed. The working volume of the entire reactor vessel is available for the gas, solid and liquid components, apart from that occupied by the draft tube, impeller, baffles and the like. Catalyst solids, gas bubbles and liquid solvent are separated externally to the reactor.

In the FIG. 3 embodiment, reactor vessel 40 contains a body of reactant gas bubbles-liquid solvent-solid catalyst 41 maintained in a recirculating flow pattern by impeller means 42 positioned within hollow draft tube 43. Thus, the gas-liquid-solid mixture or dispersion 41 passes downward within hollow draft tube 43 under the influence of impeller means 42, and passes upward in the annular space between hollow draft tube 43 and the walls of reactor vessel 40. Impeller means 42 has drive shaft 44 extending upward to overhead drive means 45. Oxygen reactant is injected into the recirculating mixture through oxygen inlet line 46, while hydrocarbon gas reactant is injected into said mixture through hydrocarbon inlet line 47. A preferred embodiment provides, as illustrated in said FIG. 3, for inlet lines 46 and 47 to extend into the recirculating mixture at injection points near the top, and on opposite sides of, hollow draft tube 43 so that said reactant gases are immediately drawn down the hollow draft tube 43 in a zone of high turbulence created by impeller means 42. Baffle means 48 are desirably provided at the upper end of hollow draft tube 43 to facilitate the flow of the recirculating mixture into said hollow draft tube 43 for downward passage therein. Said hollow draft tube 43 may also desirably include conically flared upper portion 43a to further facilitate the desired flow of the gas-liquid-solid mixture or dispersion down hollow draft tube 43.

Figure 4:
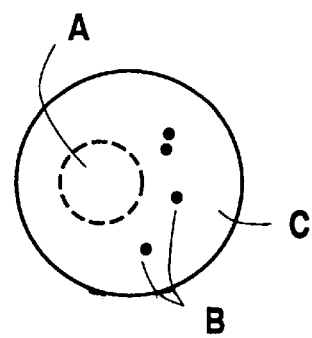
FIG. 4 is a schematic representation of solvent, catalyst particle and reactant bubble relationships in the practice of the invention.

In the practice of the invention, it is found that the dispersion of the processing components in the recirculating flow pattern maintained in the illustrated embodiments of FIG. 1–3 is of the form shown in FIG. 4 of the drawing. Thus, a bubble of desired reactants A is formed, surrounded by catalyst particles B contained in liquid solvent C. The dispersed-phase, forced-entrainment process and system of the invention results in the dispersion of a non-wetted solid catalyst and vapor-phase reactants in a recirculating body of liquid, i.e., solvent. As illustrated, the vapor-phase reactants and the solid catalyst exist as dispersed phases in the recirculating liquid, which does not directly participate in the reaction. A high degree of dispersion is achieved and provides large vapor-solid, vapor-liquid and solid-liquid interfacial areas. As a result, efficient interphase heat and mass transfer exists and enables enhanced efficiency to the achieved in the heterogeneous vapor phase catalytic processes.

It will be understood that, as in the currently preferred practice, the solvent can be employed as an inert heat transfer fluid to generate the heat transfer benefits of the invention, and the products can be recovered from the liquid-phase reactor effluent downstream of the reactor vessel. If the reaction products are insoluble in the solvent, these desired products are instead recovered from the vapor phase. Alternatively, the solvent can be used as a source of one of the reactants, e.g. the production of vinyl acetate uses ethylene, acetic acid and oxygen and the production of formaldehyde uses methanol. The gas phase reactants can strip some of the solvent into the vapor phase where it would react at the catalyst surface in the manner of normally gaseous reactants.

It will also be appreciated that various modifications can be made to the apparatus of the invention. For example, combined gas feed can be used in some applications instead of the separate gas feed lines illustrated in FIGS. 1–3 of the drawings. Premixing of the gas feeds may be desirable in some embodiments to obtain enough gas-phase mixing for reaction. The use of premixed feeds will be understood to necessitate caution to minimize explosion risks. As indicated above, the location of the reactant injection points within the reactor vessel can be varied in different embodiments of the invention. Furthermore, the impeller means for maintaining a recirculating flow pattern within the reactor vessel may be replaced by an alternative source of momentum and dispersive mixing, that is, other mechanical or other mixing means, including an injection nozzle oriented preferably downward in or above the hollow draft tube, to provide jet mixing by sonic flow of the reactants from such an injection nozzle, or other such mixing means.

It is understood that ethylene oxide (Eo) is produced, in the practice of the invention, using a silver (Ag)-based catalyst, with the reaction and EO absorption steps of conventional processing being combined into one reaction. The absorbing of EO, as it forms, into an aqueous solution prevents further oxidation, allowing higher conversion/pass and EO selectivity, and reducing or eliminating feed recycle. The operating temperature is also lowered in the practice of the invention, further improving EO selectivity. These improvements enable significant capital and operating cost savings to be realized.

Methanol is currently produced from synthesis gas in a process including (1) synthesis gas generation; (2) water shift reaction (if required); (3) methanol synthesis; (4) methanol and water condensation; and (5) methanol purification. This is a very capital intensive process, involving key issues such as synthesis gas recycle, low methanol concentrations, temperature control, and heat removal. Direct oxidation of natural gas to produce methanol has been extensively investigated, but, currently, this process is not commercially attractive because of low conversions and selectivities, and poor heat removal/recovery.

The process of the invention leads to higher conversions and selectivities, lower operating temperatures, and improved heat removal, resulting in significant capital and operating cost savings.

The invention provides a significant advance in the production of organic or inorganic chemicals by heterogeneous vapor-phase reactions, such as those referred to above. The reaction of vapor-phase components is advantageously carried out in a gas-liquid-solid mixing process in which the vapor-phase components are efficiently reacted in the presence of a solid catalyst, and the desired reaction product is readily recovered on the liquid phase. The apparatus features of the invention, including improved means to readily disperse and entrain reactant gases and solids in a recirculating body of liquid, provide enhanced interphase transport, reduced risk of explosion and combined reaction and product adsorption in a single step operation. The invention enables catalyst performance to be improved, higher catalyst selectivities and product yields to be obtained, with more efficient utilization of reactants, elimination of inerts, smaller recycle and vent-gas processing streams, and the reduced utility costs associated with smaller process streams. The invention thus represents a novel and highly desirable contribution in the art of heterogeneous, vapor phase oxidations and other reactions at the surface of a solid catalyst.

What is claimed:

1. An improved three phase mixing process for the carrying out of heterogeneous vapor phase reactions comprising:
   (a) maintaining a body of solvent comprising water and dispersed catalyst particles in a recirculating flow pattern in a reactor vessel; and
   (b) introducing a first gaseous reactant and a second gaseous reactant into said recirculating flow path to form a gas bubble-liquid solid dispersion maintained in said recirculating flow pattern, whereby a desired three phase flow pattern is maintained, with large interfacial areas between the vapor and solid phases, the vapor and liquid phases, and the solid and liquid phases, said large interfacial phases combined with the turbulent flow produced by said recirculating flow pattern, providing enhanced heat removal from the solid catalyst, rapid vapor phase transport of gaseous reactants to the solid catalyst, and efficient absorption of the reaction products in the liquid phase.

2. The process of claim 1 in which the recirculating flow pattern is maintained by axial flow impeller means.

3. The process of claim 1 in which the recirculating flow pattern is maintained by an essentially centrally positioned hollow draft tube having open ends at the top and bottom thereof, and axial flow impeller means positioned there, to cause the gas bubble-liquid-solid dispersion to pass downward through said hollow draft tube.

4. The process of claim 1 in which one gaseous reactant comprises oxygen and the second gaseous reactant comprises a hydrocarbon.

5. The process of claim 1 in which the catalyst particles comprise a porous hydrophobic support material and an active catalyst component deposited in the pores thereof, said catalyst particles comprising finely divided solids sized on the order of from about 0.1 to about 50 microns.

6. The process of claim 5 in which the catalyst concentration is from about 0.1% to about 10% by weight in said solvent.

7. The process of claim 6 in which one gaseous reactant comprises oxygen and the second gaseous reactant comprises ethylene, said catalyst having an Ag-based active catalyst component.

\* \* \* \* \*